(12) United States Patent
Ikeda

(10) Patent No.: US 7,957,573 B2
(45) Date of Patent: Jun. 7, 2011

(54) DENTAL IMAGE PROCESSING DEVICE

(75) Inventor: Yasuto Ikeda, Tokyo (JP)

(73) Assignee: Olympus Corporation, Tokyo (JP)

( * ) Notice: Subject to any disclaimer, the term of this patent is extended or adjusted under 35 U.S.C. 154(b) by 157 days.

(21) Appl. No.: 12/491,516

(22) Filed: Jun. 25, 2009

(65) Prior Publication Data

US 2009/0324072 A1    Dec. 31, 2009

(30) Foreign Application Priority Data

Jun. 30, 2008  (JP) .................................. 2008-171439

(51) Int. Cl.
*G06K 9/00* (2006.01)

(52) U.S. Cl. ....................................................... 382/128

(58) Field of Classification Search .................... 382/128
See application file for complete search history.

(56) References Cited

U.S. PATENT DOCUMENTS

| | | | | |
|---|---|---|---|---|
| 4,852,134 | A | * | 7/1989 | Kinanen et al. .................. 378/38 |
| 5,852,675 | A | * | 12/1998 | Matsuo et al. ................. 382/167 |
| 7,341,450 | B2 | * | 3/2008 | Pye et al. .......................... 433/29 |
| 2007/0036430 | A1 | | 2/2007 | Katsumata et al. |
| 2007/0140539 | A1 | * | 6/2007 | Katsumata et al. ........... 382/128 |
| 2007/0140553 | A1 | | 6/2007 | Katsumata |
| 2008/0170764 | A1 | * | 7/2008 | Burns et al. .................... 382/128 |
| 2009/0322868 | A1 | * | 12/2009 | Ikeda ............................... 348/77 |

FOREIGN PATENT DOCUMENTS

| | | |
|---|---|---|
| JP | 63-223968 A | 9/1988 |
| JP | 2001-245906 A | 9/2001 |
| JP | 2002-049694 A | 2/2002 |
| JP | 2005-130928 A | 5/2005 |
| JP | 2005-176915 A | 7/2005 |
| JP | 2005-341175 A | 12/2005 |
| JP | 2007-047045 A | 2/2007 |
| JP | 2007-190371 A | 8/2007 |

OTHER PUBLICATIONS

Japanese Office Action dated Jan. 5, 2010 issued in a counterpart Japanese Application No. 2008-171439.
Partial English translation of a Japanese Office Action dated Jan. 5, 2010 issued in counterpart Japanese Application No. 2008-171439.

* cited by examiner

*Primary Examiner* — Matthew C Bella
*Assistant Examiner* — Dennis Rosario
(74) *Attorney, Agent, or Firm* — Holtz, Holtz, Goodman & Chick, PC

(57) ABSTRACT

A subtle color difference between a tooth and a color sample is made recognizable by accentuating the color difference therebetween. The invention provides a dental image processing device including a row-of-teeth image storing unit 21 in which a row-of-teeth image is stored; an area partitioning line provided movably on the row-of-teeth image; a selected color storing unit 29 in which color information for correcting the color of the row of teeth is stored; a color correction unit 30 that corrects the color of the row of teeth, using the color information stored in the color selection storing unit 29, at least in one area of the plurality of areas of the row-of-teeth image divided by the area partitioning line; and a display control unit 31 that displays the row-of-teeth image corrected by the color correction unit 30.

11 Claims, 8 Drawing Sheets

DENTAL IMAGE PROCESSING DEVICE

BACKGROUND OF THE INVENTION

1. Field of the Invention

The present invention relates to a dental image processing device, system, and method for carrying out processing of a dental image of a patient, such as color correction, and to a computer-readable recording medium with a dental image processing program recorded therein.

This application is based on Japanese Patent Application No. 2008-171439, the content of which is incorporated herein by reference.

2. Description of Related Art

Composite resins have been conventionally used as dental filler for filling a cavity formed in a tooth due to, for example, caries. In filling with composite resins, for example, a dentist visually compares the color of a patient's tooth and the color of color samples and selects a color sample having the color closest to the patent's tooth. Each color sample is provided with a table specifying a recommended color combination for the composite resins to be used for filling, and the dentist selects the color of composite resin to be used for filling by referring to the table corresponding to the selected color sample and performs treatment therewith. Color samples in this case are, for example, ceramic pieces, bearing different colors, that are manufactured in the shape of teeth.

In addition, in treatment using the ceramic crown method, for example, a dentist visually compares the color of a patient's tooth to the color of color samples known as "shade guides", selects a color sample having the color closest to the patient's tooth, and performs treatment using a prosthesis prepared based on the selected color sample.

The color samples described above are, for example, ceramic pieces, bearing different colors, that are manufactured in the shape of teeth.

Furthermore, in order to reduce the burden on dentists associated with the above-described selection of color samples and so forth, a device has been proposed that aids in the color selection of color samples by providing a function of automatically selecting a color sample having the most similar color to a tooth (for example, refer to Japanese Unexamined Patent Application, Publication No. 2007-190371).

In addition, a device has been proposed that realizes highly precise color reproducibility by correcting the color of a row of teeth using a multiband image of teeth (for example, refer to Japanese Unexamined Patent Application, Publication No. 2005-341175).

BRIEF SUMMARY OF THE INVENTION

However, the invention disclosed in Japanese Unexamined Patent Application, Publication No. 2005-341175 has a problem in that evaluation of a subtle difference between a tooth and color samples is difficult because the color of the teeth ends up being corrected over an entire row of teeth based on a multiband image of the teeth.

The present invention has been conceived in light of the above-described situation, and an object thereof is to provide a dental image processing device, system, and method that are capable of making a subtle color difference between a tooth and color samples recognizable by accentuating the color difference therebetween and a computer-readable recording medium with a dental image processing program recorded therein.

A first aspect of the present invention is a dental image processing device including a first storage unit in which a row-of-teeth image is stored; an area partitioning line provided movably on the row-of-teeth image; a second storage unit in which color information for correcting the color of the row of teeth in the row-of-teeth image is stored; a color correction unit that corrects the color of row of teeth, using the color information stored in the second storage unit, in at least one area of a plurality of areas in the row-of-teeth image divided by the area partitioning line; and a display control unit that displays the row-of-teeth image corrected by the color correction unit.

According to such a configuration, one row-of-teeth image can be divided into a plurality of areas and can be displayed with the divided areas each in a different color. Thus, it is possible to simultaneously compare various color differences. Furthermore, because the area portioning line is movable, even if a color difference is subtle, the color difference can be accentuated by relatively quickly and repeatedly moving this area partitioning line in a predetermined direction. Thus, a subtle color difference can be made recognizable to a user.

In the above-described dental image processing device, color information of color samples for comparing to vital teeth may be stored in the second storage unit, and the color of teeth may be the color of the vital teeth in at least one area of the plurality of the areas.

Thus, the color of row of teeth can be matched to the color of a color sample in at least one area of a row-of-teeth image and, in at least one other area, the color of the row of teeth can be matched to the color of a patient's vital teeth. Accordingly, the color of vital teeth and the color of the color sample can be simultaneously compared. Furthermore, because the area portioning line is movable, even if a color difference is subtle, the color difference can be accentuated by relatively quickly and repeatedly moving this area partitioning line in a predetermined direction. As a result, it is possible to select the most suitable color sample having the color closest to the color the vital teeth.

In the above-described dental image processing device, a third storage unit, in which multiband images of vital teeth are stored, is provided when the row-of-teeth image stored in the first storage unit is an RGB image may be provided, and the color correction unit may correct the color of the row of teeth in the row-of-teeth image or the entire row-of-teeth image stored in the first storage unit using multiband images of the vital teeth stored in the third storage unit, before the color correction using the color information stored in the second storage unit is carried out.

Because a multiband image has greater color reproducibility than an RGB image, the color of a row-of-teeth image can be made even closer to the actual color by correcting the row-of-teeth image, which is an RGB image, using this multiband image. Thus, the color of the vital teeth that is close the actual color and the color of the color sample can be compared.

In the above-described dental image processing device, a gum portion in the row-of-teeth image may be excluded from the correction area of the color correction using the color information stored in the second storage unit.

In this way, by not carrying out color correction of the gum portion based on the color information stored in the second storage unit, the color of the gum portion can be made the same over the entire image in spite of the division into a plurality of areas by the area partitioning line. Accordingly, it is possible to accentuate the color difference in the tooth portion.

A second aspect of the present invention is a dental image processing system including an image acquisition device that acquires an image of the inside of an oral cavity; and a dental image processing device that processes the image captured by the image acquisition device, wherein the dental image processing device includes a first storage unit in which an image of a patient's row of teeth obtained by the image acquisition device is stored; an area partitioning line provided movably on the row-of-teeth image; a second storage unit in which color information for correcting the color of row of teeth in the row-of-teeth image is stored; a color correction unit that corrects the color of row of teeth, using the color information stored in the second storage unit, in at least one area of a plurality of areas in the row-of-teeth image divided by the area portioning line; and a display control unit that displays the row-of-teeth image corrected by the color correction unit.

A third aspect of the present invention is a dental image processing method including dividing a row-of-teeth image into a plurality of areas with a movably provided area partitioning line; correcting the color of teeth, based on predetermined color information, in at least one area of the plurality of divided areas; and displaying the corrected row-of-teeth image.

A fourth aspect of the present invention is a computer-readable recording medium with a dental image processing program stored therein for making a computer execute a process of dividing a row-of-teeth image into a plurality of areas with a movably provided area partitioning line; a process of correcting the color of teeth, based on predetermined color information, in at least one area of the plurality of divided areas; and a process of displaying the corrected row-of-teeth image.

The present invention affords an advantage in that a subtle color difference between a tooth and color samples can be made recognizable by accentuating the color difference therebetween.

DETAILED DESCRIPTION OF THE INVENTION

Figure 1:
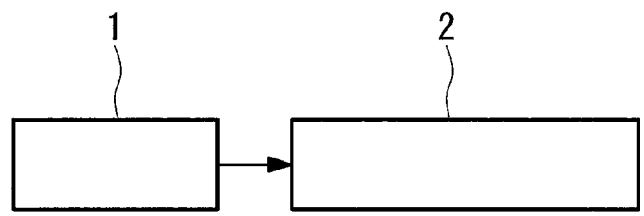
FIG. 1 is an overall configuration diagram of a dental image processing device according to an embodiment of the present invention.

Embodiments of a dental image processing device, a dental image processing system, a dental image processing method, and a computer-readable recording medium with a dental image processing program recorded therein of the present invention will be described below, referring to the drawings.

As shown in FIG. 1, a dental image processing system according to an embodiment of the present invention is configured having an image acquisition device 1 and a dental image processing device 2.

The image acquisition device 1 is, for example, an image acquisition device 1 disclosed in Japanese Unexamined Patent Application, Publication No. 2007-190371, having a normal image acquisition mode for obtaining RGB images, which is a function of a normal digital camera, and a multiband image acquisition mode.

In the multiband image acquisition mode, a plurality of light sources, built into the image acquisition device 1, that individually emit light of different wavelength bands are made to emit light in succession, and a plurality of RGB images are obtained by irradiating a subject in succession with light having different wavelength bands. Then, a B (blue) image is selected from the RGB image obtained when the light source that emits light in a wavelength band whose center wavelength is blue is activated; a G (green) image is selected from the RGB image obtained when the light source that emits light in a wavelength band whose center wavelength is green is activated; a R (red) image is selected from the RGB image obtained when the light source that emits light in a wavelength band whose center wavelength is red is activated; and the selected R image, G image, and B image are combined to produce a multiband image. In this case, it is preferable that the number of wavelength bands of light emitted from the plurality of light sources be four or greater.

Of the two image acquisition modes described above, the normal image acquisition mode is used when acquiring an image of sites over a wide area, such as an entire row of teeth of a patient, and an entire jaw. The multiband image acquisition mode, on the other hand, is used when accurately measuring the color of one or two teeth of a patient, i.e. when carrying out colorimetry of a tooth.

In the present embodiment, for example, an image of entire row of teeth of a patient is acquired by the image acquisition device 1 in the normal image acquisition mode, and images of individual teeth of the patient are acquired using the multiband image acquisition mode.

The acquired image of the entire row of teeth and the multiband images of the individual teeth, obtained by the image acquisition device 1, are transmitted to the dental image processing device 2 via a transmission medium, etc. and are stored in a database included in the dental image processing device 2. Note that the acquired image may be stored in the dental image processing device 2 via an external storage device such as a USB memory.

Figure 2:
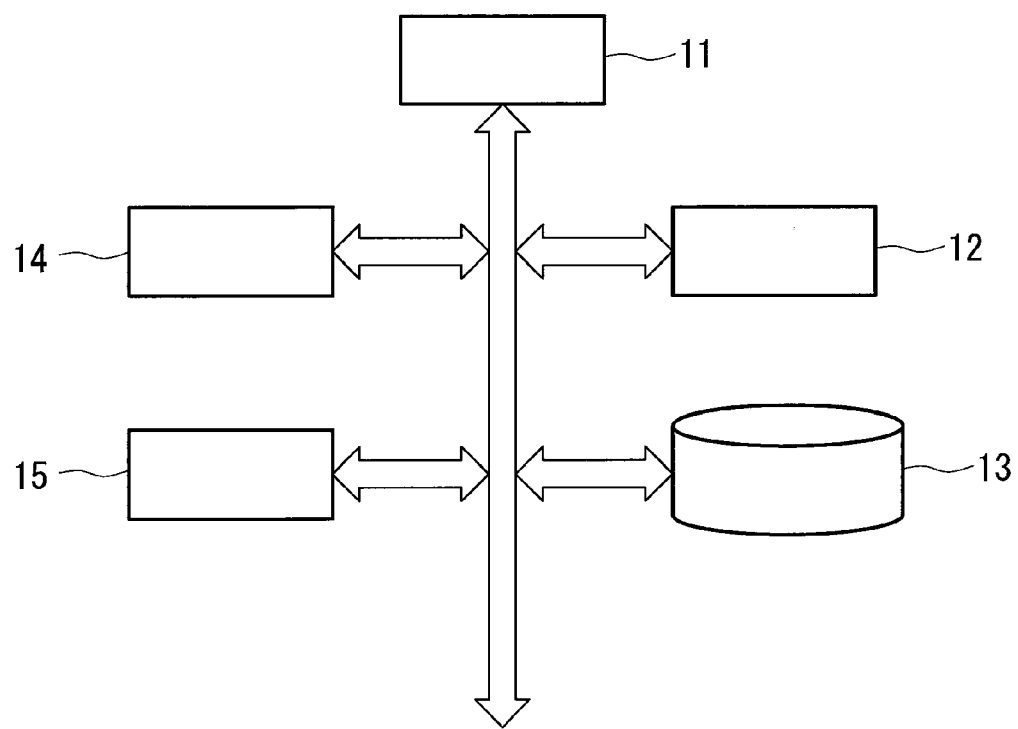
FIG. 2 is a diagram showing a hardware configuration of the dental image processing device according to an embodiment of the present invention.

The dental image processing device 2 is a computer system (calculating system), which is configured having, for example, as shown in FIG. 2, a CPU (Central Processing Unit) 11; a main storage device 12, such as RAM (Random Access Memory); a ROM (Read Only Memory); an auxiliary storage device 13; an input device 14, such as a keyboard and a mouse; and a display device 15, such as a liquid crystal display.

The auxiliary storage device 13 is a computer-readable recording medium, for example, a magnetic disk, a magneto optical disk, a CD-ROM, a DVD-ROM, or a semiconductor memory. Various programs, such as a dental image processing program, are stored in the auxiliary storage device 13, and the CPU 11 reads out a program from the auxiliary storage device 13 to the main storage device 12, such as a RAM, and executes it, thus realizing the processing of individual units described below.

Figure 3:
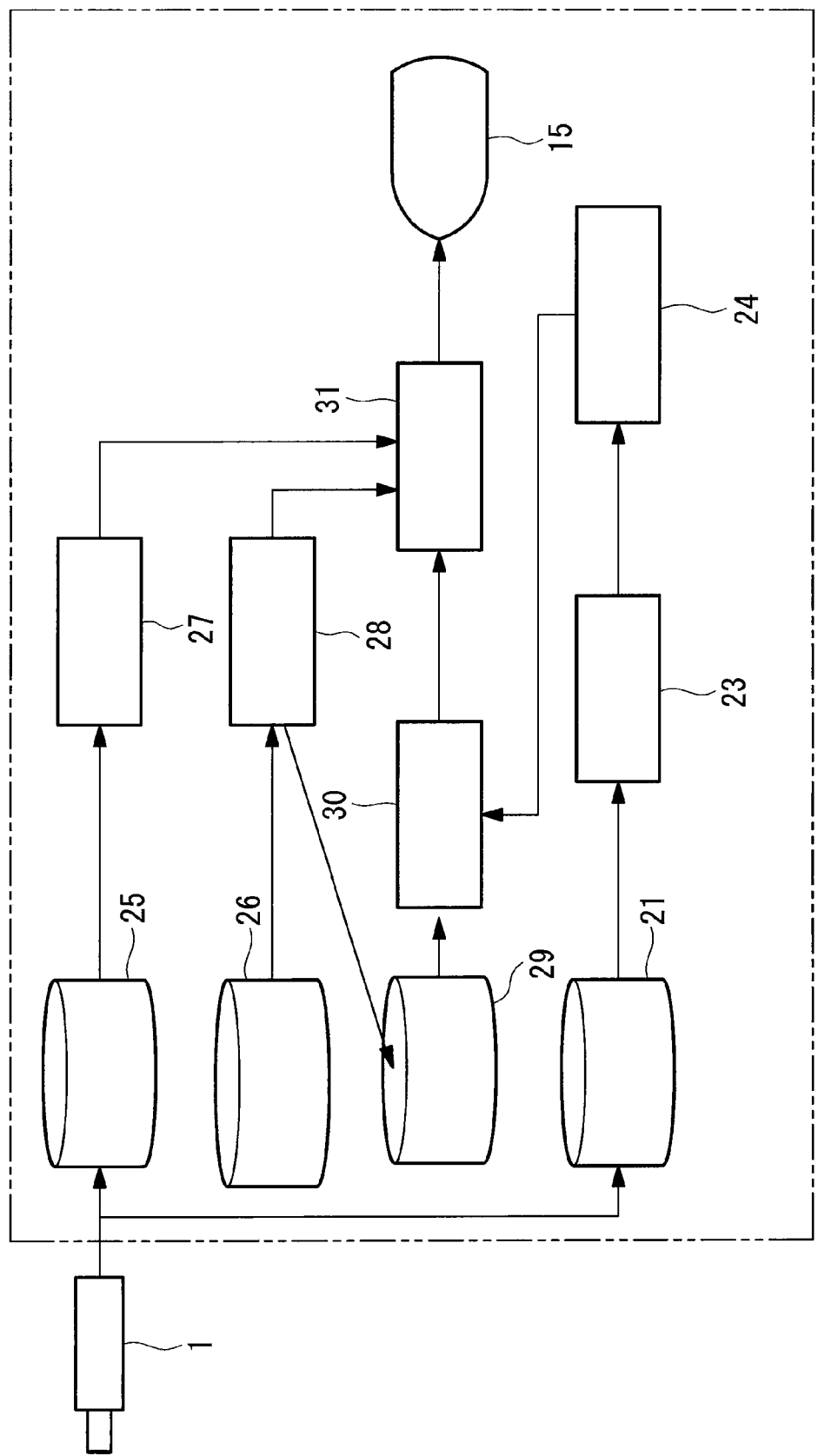
FIG. 3 is a functional block diagram of a dental image processing device according to an embodiment of the present invention.

FIG. 3 is a functional block diagram showing a breakdown of functions provided in the dental image processing device 2. As shown in FIG. 3, the dental image processing device 2 is configured mainly having a row-of-teeth image storing unit (first storage unit) 21, a teeth-gum boundary extraction unit 23, an area partition processing unit 24, a multiband image storing unit (third storage unit) 25, a shade guide storing unit 26, a first tooth selection unit 27, a second tooth selection unit 28, a color selection storing unit (second storage unit) 29, a color correction unit 30, and a display control unit 31.

The row-of-teeth image storing 21 stores an image of a patient's row of teeth obtained by the image acquisition device 1 in the normal image acquisition mode. The row-of-teeth image, in this case, is an RGB color image.

The teeth-gum boundary extraction unit 23 extracts a boundary that separates the area of the teeth from other areas (gums, etc.) in a row-of-teeth image. As for the detection of the boundary between the teeth and the gums, for example, the boundary between the gums and the teeth may be automatically extracted by executing a built-in teeth-gum boundary detection program, or, for example, the boundary may be designated by having the row-of-teeth image displayed once on the display unit 15 and having a dentist etc. trace the boundary between the gums and the teeth using a pointing pen etc.

A known technique can be employed as the method for detecting the teeth-gum boundary, and the method is not particularly limited. For example, teeth are close to white in color, whereas gum is close to red in color; therefore, it is possible to easily detect the boundary between the teeth and the gum by detecting sites with large color differences.

When a user operates the unshown input device 14 (see FIG. 2) thereby moving an area partitioning line L (see FIG. 4), described later, the area partition processing unit 24 partitions a row-of-teeth image into a plurality of areas based on movement information of the area partitioning line L and outputs partitioned area information to the color correction unit 30. In this embodiment, it is assumed, as an example, that a single area partitioning line L is provided on a row-of-teeth image. In addition, for example, the area partitioning line L, as its initial setting, is set at the center of the row-of-teeth image.

A plurality of tooth images obtained by the image acquisition device 1 in the multiband image acquisition mode are stored in the multiband image storing unit 25 in association with tooth numbers thereof. In this case, a tooth number is a number that indicates the location of the tooth in a row of teeth.

Reference color information and image information of each shade guide (color sample) are stored in the shade guide storing unit 26 in association with an identification number thereof. In this case, the "shade guides" refer to, for example, ceramic pieces that differ in color from each other and that are manufactured into tooth shapes; the reference color information refers to information obtained with respect to a reference area when images of individual shade guides are captured in the multiband image acquisition mode, for example, colorimetry values (such as RGB values, L*a*b values, CMYK values, XYZ values, L*u*v values, and L*C*h values), reflection spectra, or spectral radiant intensities; and the image information refers to, for example, resulting multiband images when images of each shade guide are acquired in the multiband image acquisition mode.

When a user operates the unshown input device 14 thereby selecting one of the multiband images stored in the multiband image storing unit 25, the first tooth selection unit 27 obtains the selected image of a tooth from the multiband image storing 25 and outputs the image to the display control unit 31.

When a user operates the unshown input device 14 thereby selecting one of the shade guides stored in the shade guide storing unit 26, the second tooth selection unit 28 obtains the selected shade guide from the shade guide storing unit 26, outputs the image information to the display control unit 31, and outputs the reference color information thereof to the selected color storing unit 29.

The selected color storing unit 29 stores the reference color information of the shade guide output from the second tooth selection unit 28. The reference color information includes, for example, colorimetry values, such as RGB values, L*a*b values, CMYK values, XYZ values, L*u*v values, and L*C*h values, reflection spectra, or spectral radiant intensities.

The color correction unit 30 corrects the color of the teeth in one of the areas partitioned by the area partitioning line L in the row-of-teeth image input from the area partition processing unit 24, based on the reference color information stored in the selected color storing unit 29, and outputs the corrected row-of-teeth image to the display control unit 31. In this embodiment, in the row-of-teeth image shown in FIG. 4, the entire row of teeth in the second area are corrected based on the reference color information stored in the selected color storing unit 29

Thus, it is possible to match the color of the teeth in the second area of the row-of-teeth image to the reference color information of the shade guide stored in the selected color storing unit 29; as for the color of the teeth in the first area, the color of the patient's teeth can be used.

More specifically, the color correction unit 30 carries out the color correction using methods such as the one described below. Here, as one example, a case will be described wherein the color correction is carried out using L*a*b values as the reference color information.

First, the color correction unit 30 converts the color space of the entire row of teeth in the second area (see FIG. 4), which is the area to be color corrected, from the RGB space to a L*a*b space, then calculates average colorimetry values ($L_s^*$, $a_s^*$, and $b_s^*$), and carries out color correction by leaving the lightness $L_s^*$ of the calculated average colorimetry values ($L_s^*$, $a_s^*$, and $b_s^*$) unmodified, while replacing the colors ($a_s^*$, and $b_s^*$) with the colors of the shade guide ($a^{*'}$ and $b^{*'}$) stored in the selected color storing unit 29. Thus, it is possible to match the color of row of teeth in one area of the row-of-teeth image to the colors of the shade guide.

Note that, although an example wherein the color correction is carried out using the L*a*b values is given in the above-described explanation, it is not limited to this. For example, color correction may be carried out using other colorimetry values, such as CMYK values, XYZ values, L*U*V values, and L*C*h values, reflection spectra, or spectral radiant intensities. Further, although the lightness L* is not replaced in the above-described example, the lightness L* may also be replaced in a similar manner.

Figure 4:
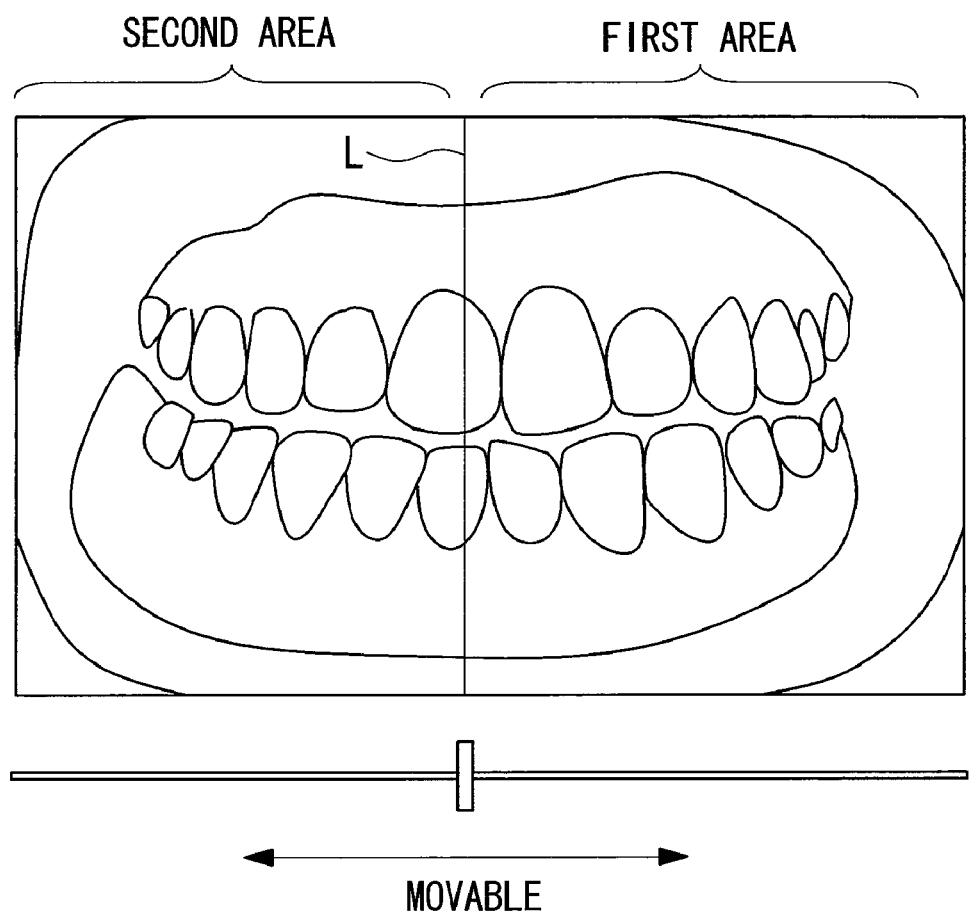
FIG. 4 is a diagram for explaining an area partitioning line that divides a row-of-teeth image and areas for color correction.

The display control unit 31 displays respective images input from the first tooth selection unit 27, the second tooth selection unit 28, and the color correction unit 30 in respective predetermined areas of the display device 15. In this case, as shown in FIG. 4, the display control unit 31 displays the area partitioning line L, which is repeatedly movable in a predetermined direction, on the row-of-teeth image displayed on the display device 15. In this embodiment, an area partitioning line L, which is freely movable in the left-right direction, is displayed.

This area partitioning line L can be freely moved by the user operating the input unit 14. When the area partitioning line L is moved by the user, movement information thereof is transmitted to the area partition processing unit 24, and new area information is output from the partition processing unit 24 to the color correction unit 30.

Then, each time the area partitioning line L is moved, the area partition processing unit 24 transmits new area information to the color correction unit 30, and therefore, color correction of the row of teeth is carried out depending on the position of the area partitioning line L at that time.

Next, the operation of the above-described dental image processing system will be described.

Figure 5:
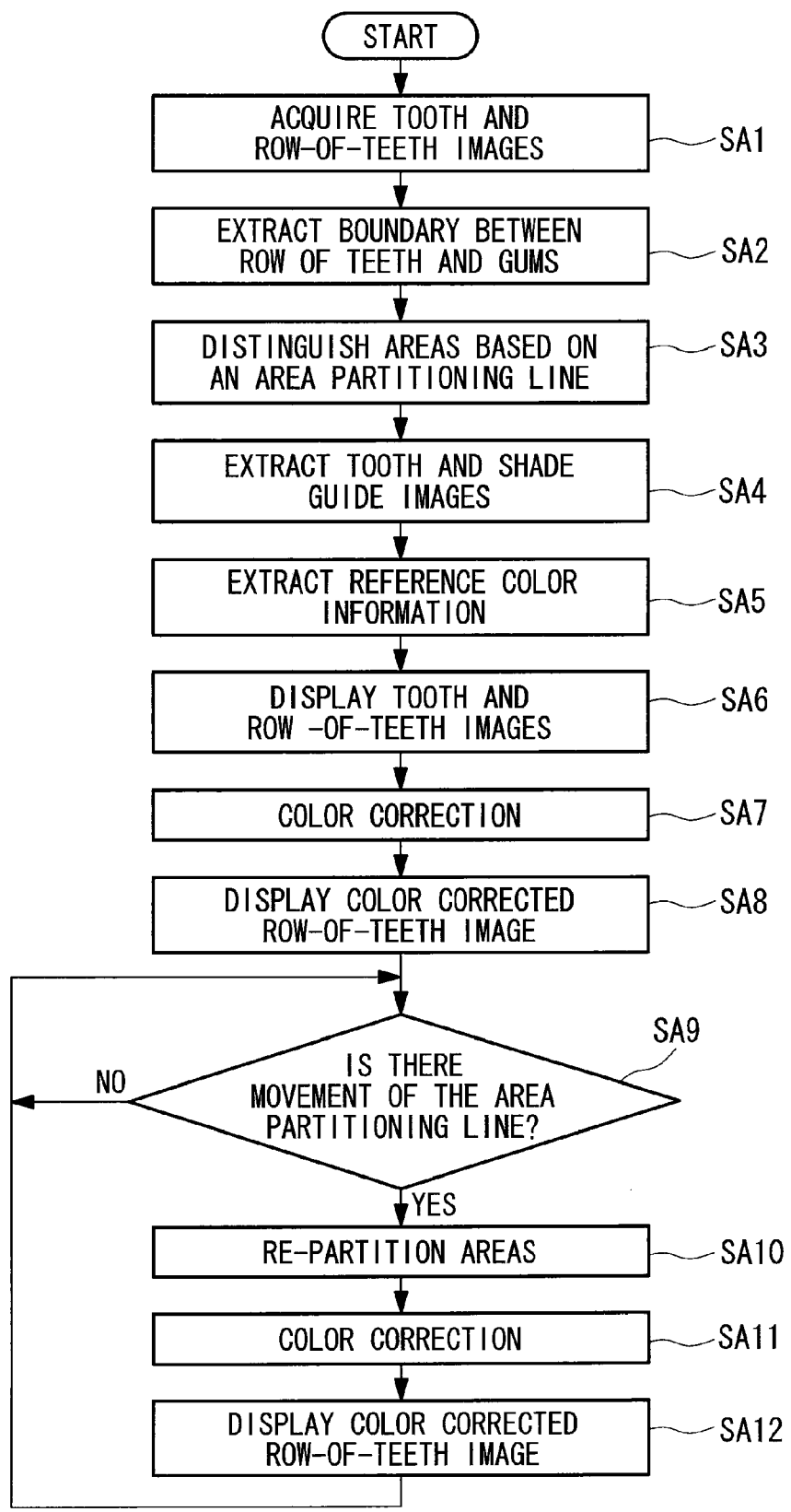
FIG. 5 is a flowchart showing a processing procedure of the dental image processing device according to an embodiment of the present invention.

First, images of the patient's teeth are acquired by a dentist using the image acquisition device 1 (Step SA1 in FIG. 5). Specifically, an image of the patient's row-of-teeth is acquired using the normal image acquisition mode, and images of individual teeth of the patient are acquired in the multiband image acquisition mode. These images obtained by image acquisition are transmitted from the image acquisition device 1 to the dental image processing device 2.

In the dental image processing device 2, the acquired multiband images of individual teeth are stored in the multiband image storing unit 25 in association with corresponding tooth numbers, and the row-of-teeth image is stored in the row-of-teeth image storing unit 21.

Next, the row-of-teeth image is read out from the row-of-teeth image storing unit 21 by the teeth-gum boundary extraction unit 23, and the boundary between the teeth and the gums in this row-of-teeth image is extracted (Step SA2); then, a row-of-teeth image with the teeth-gum boundary information added thereto is output to the area partition processing unit 24. The area partition processing unit 24 divides the row-of-teeth image with the teeth-gum boundary information added thereto into two areas based on the position of the area partitioning line L set in the initial state and outputs the row-of-teeth image and individual area information to the color correction unit 30 (Step SA3).

On the other hand, when one of teeth stored in the multiband image storing unit 25 is selected and one of the shade guides stored in the shade guide storing unit 26 is selected, by the user operating the input device 14, the first tooth selection unit 27 reads out the multiband image of the selected tooth from the multiband image storing unit 25 and outputs it to the display control unit 31, whereas the second tooth selection unit 28 reads out the image of the selected shade guide and outputs it to the display control unit 31 (Step SA4). Furthermore, the second tooth selection unit 27 reads out the reference color information for the selected shade guide from the shade guide storing unit 26 and outputs it to the selected color storing unit 29 (Step SA5).

Figure 6:
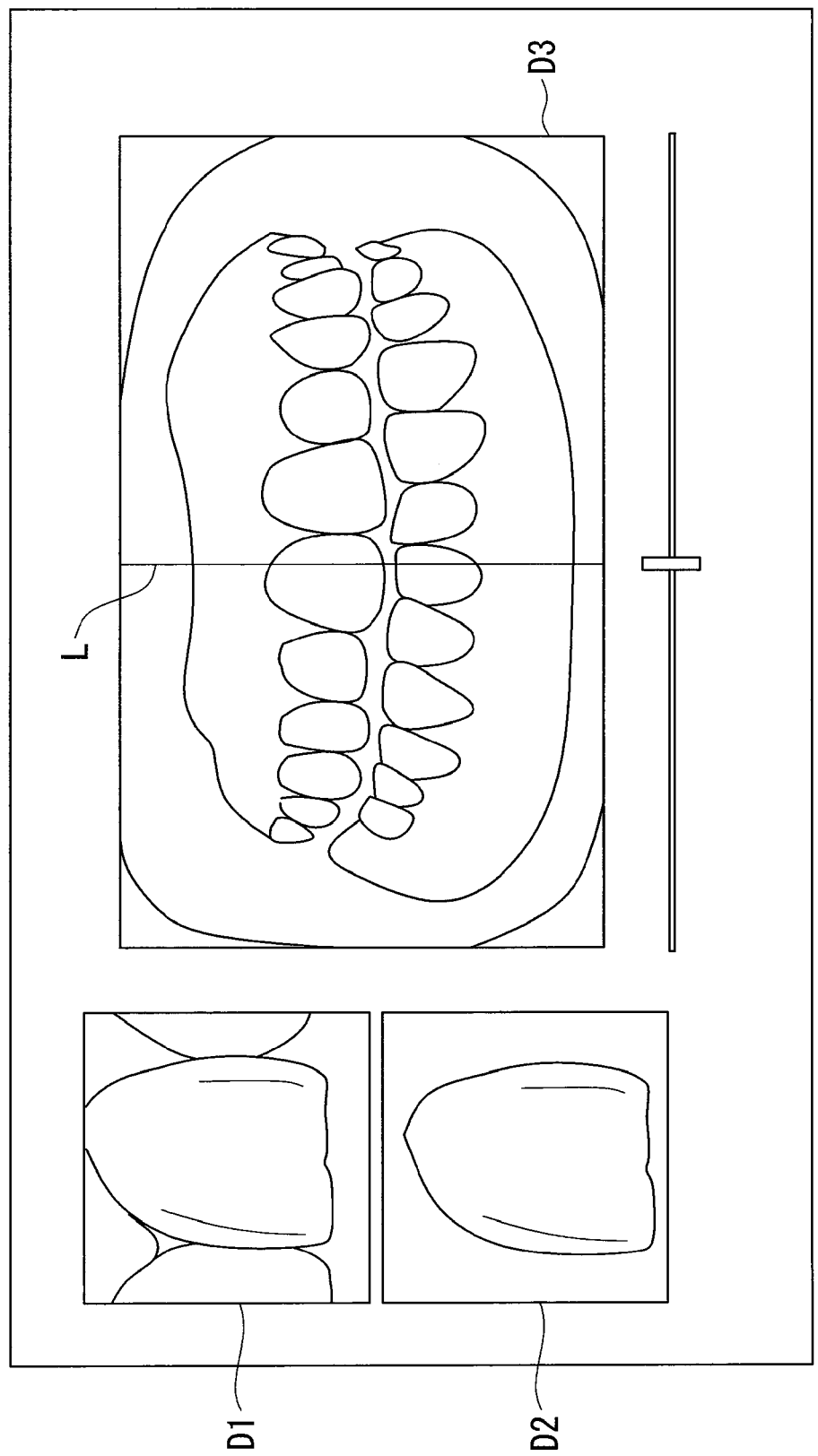
FIG. 6 is a diagram showing an example of a display screen.

The display control unit 31 displays the tooth image input from the first tooth selection unit 27 in the predetermined display area on the display device 15 (display area D1 in FIG. 6) and displays the image of the shade guide input from the second tooth selection unit 28 in the predetermined display area on the display device 15 (display area D2 in FIG. 6).

Next, the color correction unit 30 carries out color correction (Step SA7). Thus, the entire row of teeth in the second area of the row-of-teeth image are color corrected based on the reference color information of the shade guide stored in the selected color storing unit 29. The color corrected row-of-teeth image is output to the display control unit 31. Thus, the corrected row-of-teeth image is displayed in the predetermined display area (display area D3 in FIG. 6) on the display device 15 by the display control unit 31 (Step SA8). In addition, the area partitioning line L, which is movable in the left-right direction, is displayed on the row-of-teeth image.

By carrying out the above processing, as shown in FIG. 6, a row-of-teeth image in which the color of row of teeth in the second area matches the color of the shade guide is displayed on the display device 15.

In such a display screen, when the user moves the area partitioning line L left and right ("Yes" in Step SA9), movement information thereof is input to the area partition processing unit 24, the row-of-teeth image is divided into two areas depending on the new position of the area partitioning line L, and the new area information is transmitted to the color correction unit 30 (Step SA10). Thus, color correction is carried by the color correction unit 30 according to the new area information (Step SA11), and the display screen is updated with the new row-of-teeth image (Step SA12).

Then, each time the area partitioning line L is moved, the processing from Step SA8 to Step SA11 described above is repeated; therefore, the display device 15 displays a row-of-teeth image that is always color corrected based on the newest area partitioning.

In addition, the color information of the shade guide to be stored in the selected color storing unit 29 can also be changed as needed. For example, a shade guide to be selected as the second tooth can be changed by user operating the input device 14. Thus, the image of the shade guide newly selected by the second tooth selection unit 27 and the reference color information thereof are read out from the shade guide storing unit 25, and the reference color information and the like stored in the selected color storing unit 29 is updated.

As explained above, with the dental image processing device and method thereof, and the dental image processing system according to this embodiment, one row-of-teeth image can be divided into a plurality of areas and can be displayed with each area having different tooth colors. Thus, it is possible to simultaneously compare various color differences. Furthermore, because the above described area partitioning line L is movable, even a subtle color difference can be accentuated by repeatedly moving the area partitioning line L in a predetermined direction. As a result, the color difference from a patient's vital tooth is checked by repeatedly moving the area partitioning line L left and right, while updating the reference color information of the shade guide to be stored in the selected color storing unit 29; therefore, the most suitable shade guide having the closest color to the color of the patient's tooth can be selected.

Figure 7:
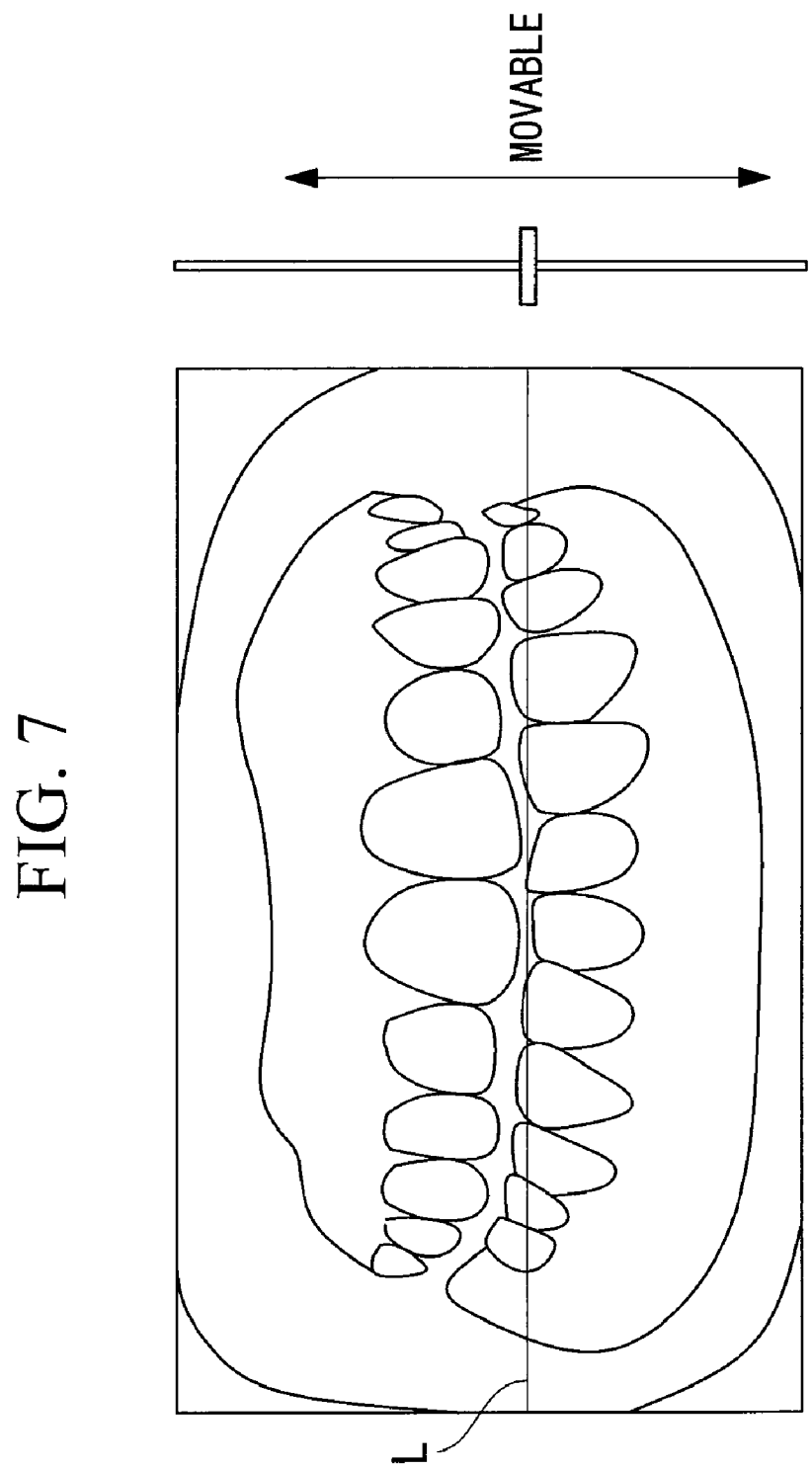
FIG. 7 is a diagram showing another example of the placement of the area partitioning line.

Note that, in the case described for the above-described embodiment, the area partitioning line L is movable in the left and right directions on the screen; however, as shown in FIG. 7, it may be movable in the up and down directions on the screen.

In addition, a plurality of area partitioning lines L may be provided. For example, at least one area partitioning line that is movable in the left-right direction and at least one area partitioning line that is movable in the up-down direction may be provided. By providing a plurality of area partitioning lines in this way, it is possible to divide a row-of-teeth image into two or more areas. In this case, shade guide colors can be set for individual areas, and therefore, it is possible to simultaneously compare a plurality of shade guide colors to the color of a vital tooth.

In addition, the number of area partitioning lines to be set may be changed by the user.

Figure 8:
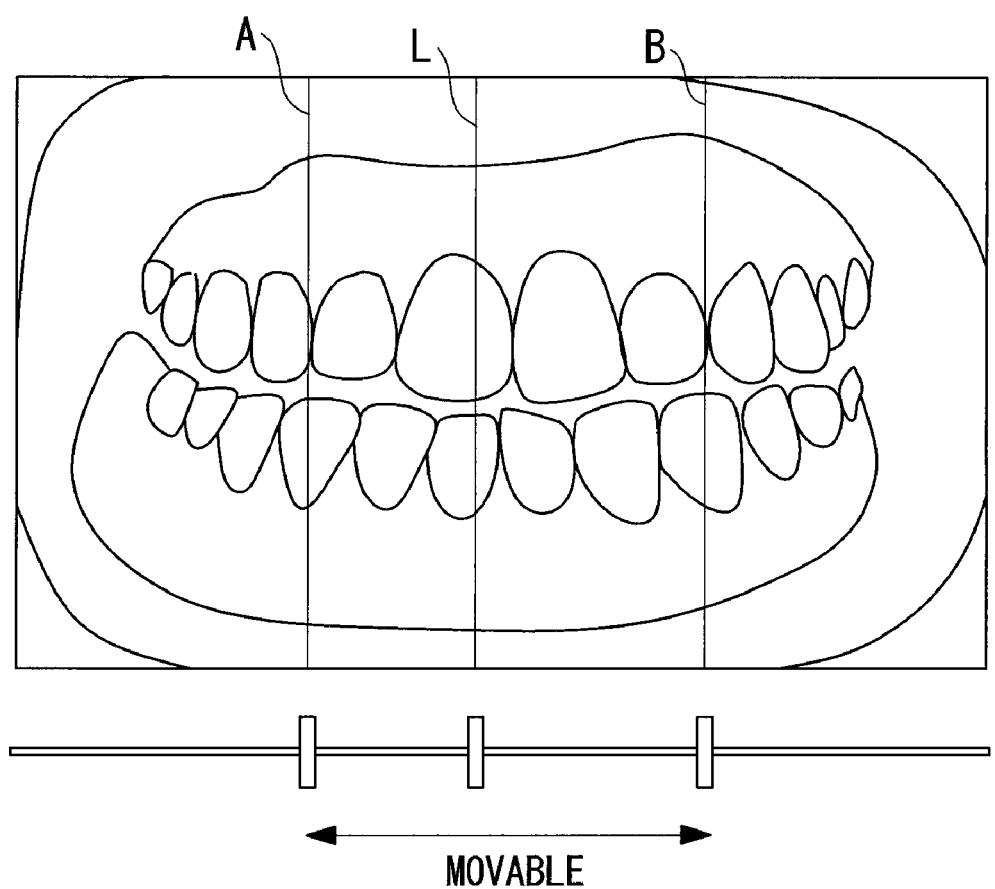
FIG. 8 is a diagram explaining a movement range setting line and a movement range of the area partitioning line.

In addition, as shown in FIG. 8, movement range setting lines A and B for restricting the movement range of the area partitioning line L may be provided, and the area partitioning line L is repeatedly movable within this movement range. In this case, the movement range setting lines A and B may also be set so that the user can move them.

Further, in this embodiment, the teeth in at least one area show the color of vital teeth, i.e. the unmodified color of the row-of-teeth image; however, alternatively, the color of the entire row-of-teeth image may be color corrected based on the multiband images of teeth stored in the multiband image storing unit 26.

As described above, in this embodiment, row-of-teeth images are obtained in the normal image acquisition mode and images of individual teeth are obtained in the multiband image acquisition mode. A multiband image has superior color reproducibility compared to an ordinary RGB color image. Therefore, the color reproducibility of the entire row-of-teeth image can be enhanced by correcting the color of the row-of-teeth image based on the color information of the multiband image.

Details of correcting a row-of-teeth image based on a multiband image will be described below.

In this case, a row-of-teeth image and a multiband image of a tooth to be corrected are displayed on the display device 15 in advance, and the user designates the range to serve as the reference for color correction.

Figure 9:
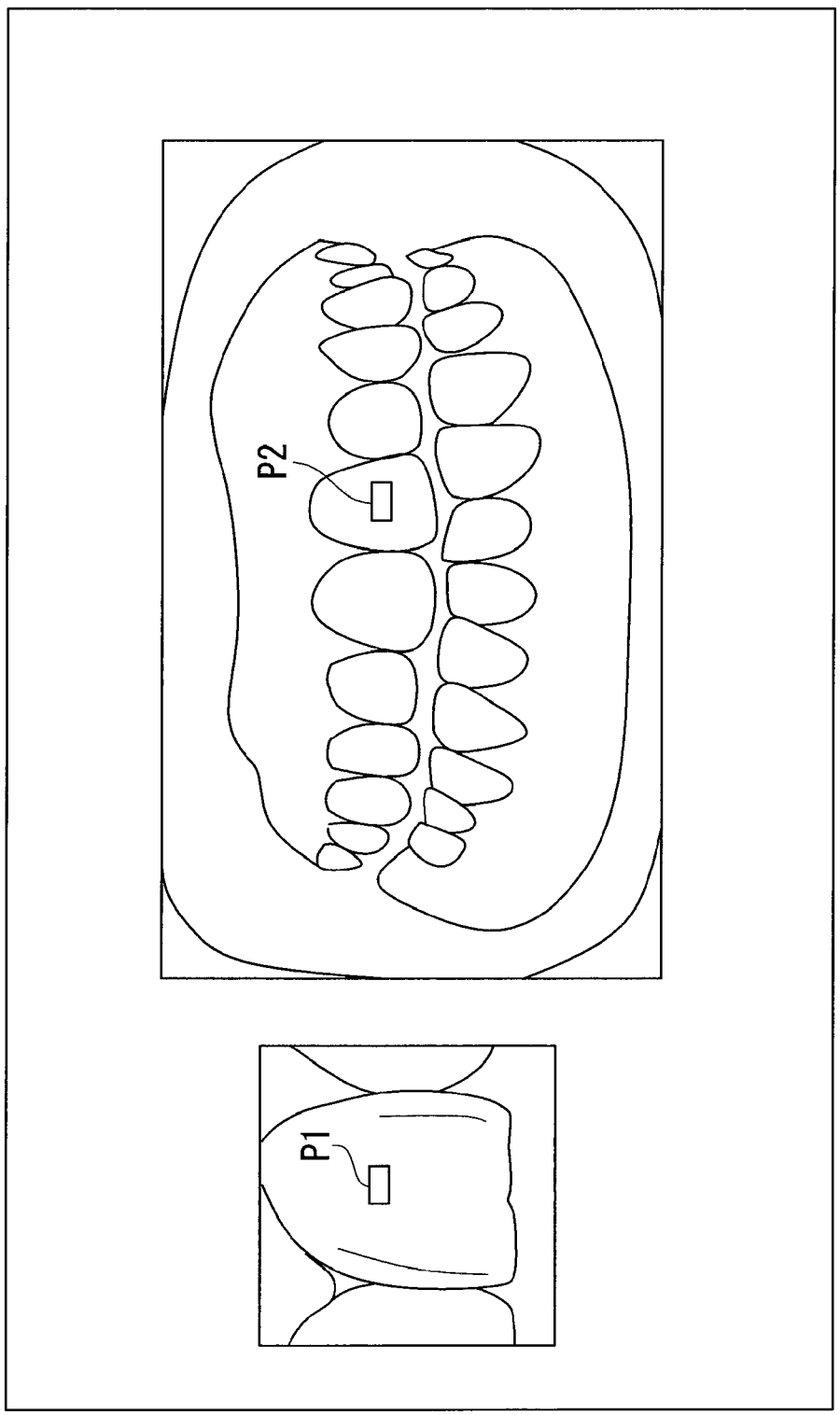
FIG. 9 is a diagram for explaining color correction of the entire row-of-teeth image.

For example, in the display screen shown in FIG. 9, when the user selects a portion P1 of the multiband image of a tooth and a portion P2 of a tooth that composes a row-of-teeth image, colorimetry values ($L_1^*$, $a_1^*$, $b_1^*$) of the area P1 selected in the multiband image and colorimetry values ($L_2^*$, $a_2^*$, $b_2^*$) of the area P2 selected in the row-of-teeth image are determined, and then a color difference between the two areas is computed.

Next, color correction of the entire row-of-teeth image is carried out so as to make the color difference zero. In other words, color correction that makes the above-described color difference zero is applied to the entire row-of-teeth image. Specifically, a correction factor matrix for converting the colorimetry values ($L_1^*$, $a_1^*$, $b_1^*$) to the colorimetry values ($L_2^*$, $a_2^*$, $b_2^*$) is determined, and the color correction of the row-of-teeth image is carried out by multiplying all pixels of the row-of-teeth image by this correction factor matrix.

Thus, the color of a tooth in the row-of-teeth image can be matched to the color of a tooth in the multiband image, and the color reproducibility can be enhanced by correcting the color of the gum in a similar manner.

In this way, because the row-of-teeth image and the multiband image of a tooth are images obtained from the same patient, the color of the gum and the color of the tooth are both obtained from the same subject. Therefore, unlike the case described above wherein the color correction is carried out based on the color of the shade guide, it is possible to have colors even closer to the actual colors in each area of the row-of-teeth image by carrying out color correction not only in the teeth but also in gum portions.

After correcting the entire row-of-teeth image based on the multiband image in this way, the above-described processing may be carried out using this row-of-teeth image.

What is claimed is:

1. A dental image processing device comprising:
a first storage unit in which a row-of-teeth image is stored;
a display control unit that displays an area partitioning line movably on the row-of-teeth image;
a second storage unit in which color information for correcting a color of a row of teeth in the row-of-teeth image is stored; and
a color correction unit that corrects the color of the row of teeth, using the color information stored in the second storage unit, in at least one area of a plurality of areas in the row-of-teeth image divided by the area partitioning line;
wherein the display control unit displays the row-of-teeth image corrected by the color correction unit.

2. The dental image processing device according to claim 1, wherein color information of color samples for comparing to vital teeth is stored in the second storage unit, and a color of teeth in at least one area of the plurality of areas is a color of the vital teeth.

3. The dental image processing device according to claim 1, wherein the row-of-teeth image stored in the first storage unit is an RGB image, and a third storage unit is provided in which multiband images of vital teeth are stored; and
wherein the color correction unit corrects the color of the row of teeth in the row-of-teeth image stored in the first storage unit or corrects the entire row-of-teeth image stored in the first storage unit using the multiband images of the vital teeth stored in the third storage unit, before the color correction using the color information stored in the second storage unit is carried out.

4. The dental image processing device according to claim 1, wherein a gum portion in the row-of-teeth image is excluded from a correction area of the color correction using the color information stored in the second storage unit.

5. A dental image processing system comprising:
an image acquisition device that acquires an image of an inside of an oral cavity; and
a dental image processing device that processes the image captured by the image acquisition device,
wherein the dental image processing device includes:
a first storage unit in which a row-of-teeth image of a row of a patient's teeth obtained by the image acquisition device is stored;
a display control unit that displays an area partitioning line movably on the row-of-teeth image;
a second storage unit in which color information for correcting a color of the row of teeth in the row-of-teeth image is stored; and
a color correction unit that corrects the color of the row of teeth, using the color information stored in the second storage unit, in at least one area of a plurality of areas in the row-of-teeth image divided by the area partitioning line;
wherein the display control unit displays the row-of-teeth image corrected by the color correction unit.

6. A dental image processing method comprising:
dividing a row-of-teeth image into a plurality of areas with a movable area partitioning line;
correcting a color of teeth, based on predetermined color information, in at least one area of the plurality of divided areas of the row-of-teeth image; and
displaying the corrected row-of-teeth image.

7. A non-transitory computer-readable recording medium with a dental image processing program stored therein that is executable by a computer to perform functions comprising:
dividing a row-of-teeth image into a plurality of areas with a movable area partitioning line;
correcting a color of teeth, based on predetermined color information, in at least one area of the plurality of divided areas of the row-of-teeth image; and
displaying the corrected row-of-teeth image.

8. A dental image processing device comprising:
a first storage unit in which a row-of-teeth image is stored;
a display control unit that displays an area partitioning line on the row-of-teeth image such that the area partitioning line is repeatedly movable;

a second storage unit in which color information for correcting a color of a row of teeth in the row-of-teeth image is stored; and a color correction unit that corrects the color of the row of teeth, using the color information stored in the second storage unit, in at least one area of a plurality of areas in the row-of-teeth image divided by the area partitioning line;

wherein the display control unit displays the row-of-teeth image corrected by the color correction unit.

9. A dental image processing system comprising:

an image acquisition device that acquires an image of an inside of an oral cavity; and a dental image processing device that processes the image captured by the image acquisition device, wherein the dental image processing device includes:

a first storage unit in which a row-of-teeth image of a row of a patient's teeth obtained by the image acquisition device is stored;

a display control device that displays an area partitioning line on the row-of-teeth image such that the area partitioning line is repeatedly movable;

a second storage unit in which color information for correcting a color of the row of teeth in the row-of-teeth image is stored; and a color correction unit that corrects the color of the row of teeth, using the color information stored in the second storage unit, in at least one area of a plurality of areas in the row-of-teeth image divided by the area partitioning line;

wherein the display control unit displays the row-of-teeth image corrected by the color correction unit.

10. A dental image processing method comprising:

dividing a row-of-teeth image into a plurality of areas with an area partitioning line which is repeatedly movable;

correcting a color of teeth, based on predetermined color information, in at least one area of the plurality of divided areas of the row-of-teeth image; and displaying the corrected row-of-teeth image.

11. A non-transitory computer-readable recording medium with a dental image processing program stored therein that is executable by a computer to perform functions comprising:

dividing a row-of-teeth image into a plurality of areas with an area partitioning line which is repeatedly movable;

correcting a color of teeth, based on predetermined color information, in at least one area of the plurality of divided areas of the row-of-teeth image; and displaying the corrected row-of-teeth image.

\* \* \* \* \*